(12) United States Patent
Kuechler et al.

(10) Patent No.: US 6,482,998 B1
(45) Date of Patent: Nov. 19, 2002

(54) PROCESS FOR CONVERTING OXYGENATES TO OLEFINS WITH DIRECT PRODUCT QUENCHING FOR HEAT RECOVERY

(75) Inventors: Keith H. Kuechler, Friendswood; James R. Lattner, Seabrook, both of TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/572,576

(22) Filed: May 17, 2000

Related U.S. Application Data (63) Continuation-in-part of application No. 09/069,403, filed on Apr. 29, 1998, now Pat. No. 6,121,504.

(51) Int. Cl.$^7$ ................................................ C07C 1/00
(52) U.S. Cl. ...................... 585/638; 585/639; 585/640; 585/910
(58) Field of Search ................................ 585/638, 639, 585/640, 910

(56) References Cited

U.S. PATENT DOCUMENTS

| | | | |
|---|---|---|---|
| 2,949,493 A | 8/1960 | Happel et al. ................ 585/640 |
| 3,998,899 A | 12/1976 | Daviduk et al. ......... 260/668 R |
| 4,044,061 A | 8/1977 | Chang et al. ............ 260/668 R |
| 4,387,263 A | 6/1983 | Vogt et al. .................... 585/640 |
| 4,440,871 A | 4/1984 | Lok et al. ..................... 502/214 |
| 4,499,327 A | 2/1985 | Kaiser ......................... 585/640 |
| 4,567,029 A | 1/1986 | Wilson et al. ................ 423/306 |
| 4,579,999 A | 4/1986 | Gould et al. ................. 585/640 |
| 4,851,606 A | * 7/1989 | Ragonese et al. ............ 585/640 |
| 4,861,743 A | 8/1989 | Flank et al. .................. 502/214 |
| 4,861,938 A | 8/1989 | Lewis et al. ................. 585/640 |
| 4,929,780 A | 5/1990 | Wright et al. ................ 585/303 |
| 5,095,163 A | 3/1992 | Barger ......................... 585/640 |
| 5,126,308 A | 6/1992 | Barger et al. ................ 502/214 |
| 5,157,181 A | 10/1992 | Stine et al. .................. 585/329 |
| 5,191,141 A | 3/1993 | Barger et al. ................ 585/640 |
| 5,714,662 A | 2/1998 | Vora et al. ................... 585/640 |
| 5,744,680 A | 4/1998 | Mulvaney, III et al. ..... 585/640 |
| 5,990,369 A | * 11/1999 | Barger et al. ................ 585/640 |

FOREIGN PATENT DOCUMENTS

| | | | |
|---|---|---|---|
| WO | WO 93/24431 | 12/1993 | |
| WO | WO 96/28408 | 9/1996 | |
| WO | WO 99/55650 | 11/1999 | ........... C07C/11/02 |

OTHER PUBLICATIONS

Chang, "Methanol Conversion to Light Olefins," *Catal. Rev.–Sci. Eng.*, 26(3 &4), pp. 323–345 (1984).
Kaeding et al., "Production of Chemicals from Methanol," *Journal of Catalysts*, vol. 64, pp. 155–64 (1980).
*Zeolites*, vol. 17, pp. 212–222 (1996).
J. Chen et al., Studies in Surface Science and Catalysts, Proceedings of the Tenth International Catalysts Society, vol. 84, pp. 17–31 (1994).

* cited by examiner

*Primary Examiner*—Marian C. Knode
*Assistant Examiner*—Tam M. Nguyen
(74) *Attorney, Agent, or Firm*—Bradley Keller; Paul LaVoie (57) ABSTRACT

The present invention relates to a process for catalytically converting a feedstock comprising an oxygenate to olefins utilizing a heat exchange device to transfer heat from at least a portion of an effluent of an oxygenate conversion reactor to the feedstock to cause at least a portion of the feedstock to vaporize.

86 Claims, 1 Drawing Sheet

FIG. 1

PROCESS FOR CONVERTING OXYGENATES TO OLEFINS WITH DIRECT PRODUCT QUENCHING FOR HEAT RECOVERY

RELATED APPLICATIONS

This application is a continuation-in-part of application Ser. No. 09/069,403, filed Apr. 29, 1998, now U.S. Pat. No. 6,121,504.

FIELD OF THE INVENTION

The present invention relates to a process for increasing the efficiency of heat recovery and improving heat integration with direct product quenching in the selective conversion of oxygenates to olefins.

BACKGROUND OF THE INVENTION

Light olefins (defined herein as ethylene, propylene, butenes and mixtures thereof) serve as feeds for the production of numerous important chemicals and polymers. Light olefins traditionally are produced by cracking petroleum feeds. Because of the limited supply and escalating cost of petroleum feeds, the cost of producing olefins from petroleum sources has increased steadily. Efforts to develop and improve olefin production technologies, particularly light olefins production technologies, based on alternative feedstocks have increased.

An important type of alternative feedstocks for the production of light olefins are oxygenates, such as alcohols, particularly methanol and ethanol, dimethyl ether, methyl ethyl ether, methyl formate, and dimethyl carbonate. Alcohols may be produced by fermentation, or from synthesis gas derived from natural gas, petroleum liquids, carbonaceous materials including coal, recycled plastics, municipal wastes, agricultural products, or most organic materials. Because of the wide variety of raw material sources, alcohol, alcohol derivatives, and other oxygenates have promise as an economical, non-petroleum feedstock source for olefin production.

The conversion of oxygenates to olefins takes place at a relatively high temperature, generally higher than about 250° C., preferably higher than about 300° C. Because the conversion reaction is exothermic, the effluent typically has a higher temperature than the initial temperature in the reactor. Many methods and/or process schemes have been proposed to manage the heat of reaction generated from the oxygenate conversion reaction inside of the reactor in order to avoid temperature surges and hot spots, and thereby to reduce the rate of catalyst deactivation and reduce the production of undesirable products, such as methane, ethane, carbon monoxide and carbonaceous deposits or coke. It would be very useful to have a process that effectively utilizes the heat of reaction contained in the products exiting the oxygenate conversion reactor, optimizes heat recovery, and reduces overall utility consumption in the conversion of oxygenates to olefins. Such a process is environmentally, economically, and commercially more attractive.

In the conventional systems, the oxygenate conversion reaction is predominantly conducted in the vapor phase using feedstocks and diluents that are usually liquid at ambient conditions. This requires supplying substantial heat to the process to boil the oxygenate feedstock prior to introducing it to the reactor, conventionally supplied by steam heat exchange or furnaces. Loss of energy is incurred in these indirect heat exchange methods, and substantial equipment is required. For steam, boilers must be built in addition to a steam/feed exchanger, and construction of a furnace is more expensive and complicated than a traditional heat exchanger. Methods are needed to improve the energy efficiency of the oxygenate conversion process and reduce the cost of providing vaporized oxygenate feedstock to an oxygenate conversion reactor.

Energy efficiency and cost of providing vaporized oxygenate feed is further complicated if utilization of a diluent is desired. The most commonly noted diluent, water/steam as disclosed in U.S. Pat. No. 5,714,662, requires substantial energy and equipment cost to generate, but has the advantage of being easily able to separate from desired light olefins (especially ethylene and propylene). Other very commonly noted diluents such as inert gases, including nitrogen, helium and even methane (see U.S. Pat. No. 5,744,680) require no energy or equipment to vaporize, but require extensive energy and equipment to separate from the desired light olefin product. Further, use of diluents can allow high total pressures while providing low oxygenate partial pressures, which can be advantageous in reducing compression energy needed in the overall (including olefin separation and recovery) oxygenate conversion process, but this benefit may be outweighed by the energy costs of boiling and separating of the diluent just noted. Proper selection of diluent composition is also needed to improve the energy efficiency in the overall process and reduce the cost of providing vaporized oxygenate feedstock to an oxygenate conversion reactor.

SUMMARY OF THE INVENTION

The present invention provides a process for converting an oxygenate to olefins with increased heat recovery and heat integration, said process comprising: heating a feedstock comprising said oxygenate having a first heat content from a first temperature to a second temperature through from one to about three stages having successively higher heat contents; contacting said feedstock at said second temperature with a catalyst comprising a molecular sieve under conditions effective to produce a deactivated catalyst having carbonaceous deposits and a product comprising said olefins, wherein said molecular sieve comprises pores having a pore diameter smaller than about 10 Angstroms and said product has a third temperature which is higher than said second temperature; quenching said product with a medium at an initial temperature and in an amount sufficient for forming a light product fraction and a heavy product fraction wherein said light product fraction comprises light olefins and said heavy product fraction has a final temperature which is higher than said first temperature by at least about 5° C.; using said heavy product fraction to provide heat at one or more of said stages to achieve said higher heat contents.

In another preferred embodiment, the process for converting an oxygenate to olefins comprises providing a feedstock comprising the oxygenate, transferring heat from at least a portion of an effluent of an oxygenate conversion reactor to the feedstock to cause at least a portion of the feedstock to vaporize and form a vaporized feedstock, and contacting the vaporized feedstock at a temperature from about 200 to about 750° C. and a pressure from 1 kPa to 100 MPa with a catalyst comprising a molecular sieve having a pore diameter smaller than 10 Angstroms, wherein the feedstock has a boiling range of no greater than about 30° C., the oxygenate conversion reactor converts at least a portion of the feedstock into the effluent, and the effluent comprises the olefins.

In another preferred embodiment, the process for converting an oxygenate to olefins comprises providing a feedstock comprising the oxygenate and a diluent, transferring heat from at least a portion of an effluent of an oxygenate conversion reactor to the feedstock to cause at least a portion of the feedstock to vaporize and form a vaporized feedstock, and separating the diluent from the effluent, wherein the feedstock has a boiling range of no greater than about 30° C., the oxygenate conversion reactor converts at least a portion of the feedstock into the effluent, and the effluent comprises the olefins.

In another preferred embodiment, the process for converting an oxygenate to olefins comprises providing a feedstock comprising the oxygenate and a diluent, transferring heat from at least a portion of an effluent of an oxygenate conversion reactor to the feedstock to cause at least a portion of the feedstock to vaporize and form a vaporized feedstock, contacting the vaporized feedstock at a temperature from about 200 to about 750° C. and a pressure from 1 kPa to 100 MPa with a catalyst comprising a molecular sieve having a pore diameter smaller than 10 Angstroms, and separating the diluent from the effluent, wherein the feedstock has a boiling range of no greater than about 30° C., the oxygenate conversion reactor converts at least a portion of the feedstock into the effluent, and the effluent comprises the olefins.

DETAILED DESCRIPTION OF THE INVENTION

The present invention provides a process for increasing heat recovery and decreasing energy and utility requirements during the conversion of oxygenates to olefins. The process involves taking the product mixture, including any unreacted oxygenate feed, from an oxygenate conversion reactor and, without fractionating the products, directly quenching the product mixture with a suitable medium, preferably water. This type of quenching hereinafter will be referred to as "direct product quench." The direct product quench removes heat from the product mixture, causing higher boiling components, such as water and unreacted oxygenate feed, to condense and form a heavy product fraction. The heavy product fraction is separated from the light product fraction comprising gaseous hydrocarbon components such as light olefins, methane, ethane, propane, and butanes. The heavy product fraction may be divided further into several fractions. The heavy production fraction, or any, or all of the several fractions may be subjected to various techniques or methods to separate the quench medium from other components. The heavy product fraction, or any, or all of the several fractions or streams produced from quench medium separations thereof, may be used to supply at least part of the heat needed to vaporize or otherwise to increase the heat content of the oxygenate feedstock, through from one to about three stages, prior to being introduced into the oxygenate conversion reactor for contacting the oxygenate conversion catalyst. These stages give the oxygenate feedstock successively higher heat content.

Most catalysts that are used in oxygenate conversion processes comprise molecular sieves, both zeolitic (zeolites) and non-zeolitic types. The present invention should achieve many of the desired improvements using substantially any molecular sieve catalyst, regardless of the structure type or pore size. Mixtures of zeolitic and non-zeolitic molecular sieves also may be used. Preferred molecular sieve catalysts for use according to the present invention comprise "small" and "medium" pore molecular sieve catalysts. "Small pore" molecular sieve catalysts are defined as catalysts with pores having a pore diameter of less than about 5.0 Angstroms. "Medium pore" molecular sieve catalysts are defined as catalysts with pores having a pore diameter in the range of from about 5.0 to about 10.0 Angstroms. "Large pore" molecular sieve catalysts are catalysts with pores having a pore diameter larger than about 10.0 Angstroms. Generally, large pore molecular sieve catalysts, without additional appropriate modifications and/or treatments, are not preferred catalysts for converting oxygenates to light olefins.

Zeolitic molecular sieve catalysts suitable for the use in the present invention with varying degree of effectiveness include, but are not necessarily limited to AEI, AFI, CHA, ERI, LOV, RHO, THO, MFI, FER, and substituted examples of these structural types, as described in W. M. Meier and D. H. Olson, *Atlas of Zeolitic Structural Types* (Butterworth Heineman—third edition, 1997), incorporated herein by reference. Preferred zeolite catalysts include but are not necessarily limited to zeolite 3A, zeolite 4A, zeolite 5A (collectively referred to hereinafter as zeolite A), ZK-5, ZSM-5, ZSM-34, erionite, chabazite, offretite, silicalite, borosilicates and mixtures thereof See Meier and Olson. These zeolites may be obtained from many companies and commercial sources such as Mobil, AMOCO, UCI, Engelhard, Aldrich Chemical Company, Johnson Matthey Company, Union Carbide Corporation, and others.

Silicoaluminophosphates ("SAPO's") are one group of non-zeolitic molecular sieves that are useful in the present invention. Suitable SAPO's for use in the invention include, but are not necessarily limited to SAPO-17, SAPO-18, SAPO-34, SAPO-44, and mixtures thereof Small pore SAPO's are preferred for producing light olefins. A preferred SAPO is SAPO-34, which may be synthesized according to U.S. Pat. No. 4,440,871, incorporated herein by reference, and *Zeolites*, Vol. 17, pp. 212–222 (1996), incorporated herein by reference. SAPO-18 may be synthesized according to J. Chen et al. *Studies in Surface Sciences and Catalysis*, Proceedings of the Tenth International Catalysis Society, Volume 84, pp 17–31 (1994).

Substituted silicoaluminophosphates (substituted SAPO's) form another class of non-zeolitic molecular sieves known as "MeAPSO's," that are suitable for use as catalysts in the present invention. MeAPSO's are described in U.S. Pat. No. 4,567,029 and U.S. Pat. No. 5,126,308, incorporated herein by reference. SAPO's with substituents incorporated after synthesis, also may be suitable for use in the present invention. Suitable substituents, "Me," include, but are not necessarily limited to nickel, cobalt, manganese, chromium, iron, zinc, strontium, magnesium, barium, and calcium. Preferred MeAPSO's include, but are not necessarily limited to NiSAPO-17, NiSAPO-34, Co-SAPO-17, Co-SAPO-34, Sr modified SAPO-17 (SrAPSO-17), Sr modified SAPO-18 (SrAPSO-18), Sr modified SAPO-34 (SrAPSO-34), SrAPSO-44, and mixtures thereof Different substituents may be incorporated during or after the synthesis of the silicoaluminophosphates.

Substituted aluminophosphates (ALPO) known as MeAPO's may also be used as the non-zeolitic molecular sieve catalysts for the present invention. MeAPO's include, but are not necessarily limited to ZnAPO, ZrAPO, TiAPO, and mixtures thereof. These molecular sieves may be synthesized according to U.S. Pat. No. 4,861,743, U.S. Pat. No. 4,567,029, and U.S. Pat. No. 5,126,308.

Because the catalyst may be used in a variety of oxygenate conversion reactors and/or under a variety of reaction conditions, it may contain binders, fillers, or other material to provide better catalytic performance, attrition resistance, regenerability, and other desired properties for a particular type reactor. When used in a fluidized bed reactor, the catalyst should be fluidizable under the reaction conditions. A catalyst may be subjected further to a variety of treatments to achieve the desired physical, mechanical, and catalytic characteristics. Such treatments include, but are not necessarily limited to calcination, milling, ball milling, grinding, spray drying, hydrothermal treatment with steam at elevated temperatures—from about 400° C. to about 800° C., acid treatment, base treatment, and combinations thereof.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof More preferred as co-feeds are a $C_4^+$ hydrocarbon mixtures, with the most preferred being $C_4^+$ hydrocarbon mixtures which are obtained from separation and recycle of reactor product.

Preferably, the oxygenate feedstock should be at least partially vaporized and contacted in a suitable oxygenate conversion reactor with the selected molecular sieve catalyst under process conditions effective to produce the desired olefins at an acceptable conversion level with desired selectivities.

The temperature employed in the conversion process may vary over a wide range depending, at least in part, on the pressure, the selected catalyst, the reactor configuration, the weight hourly space velocity, and other reaction parameters. Although not limited to a particular temperature, best results will be obtained if the process is conducted at temperatures in the range of from about 200° C. to about 750° C., preferably in the range of from about 250° C. to about 650° C., and most preferably in the range of from about 300° C. to about 600° C.

Since the oxygenate feedstock normally is stored at ambient temperatures before it is used in the conversion process, the feedstock has to be heated to a higher temperature with a much higher heat content suitable for contacting the oxygenate conversion catalyst. It is preferable to increase the heat content and/or the temperature of the feedstock through from one to about three intermediate stages, with each stage having a successively higher heat content. Many different streams in the oxygenate conversion process may be suitable sources for providing the necessary heat to increase heat contents. These streams, including those derived from the heavy product fraction from the quench tower and the streams from the fractionator separating quench medium from other components, are described in more detail below. It should be pointed out that a stream may have a higher heat content after a heat exchange even though it has a lower temperature, primarily resulting from pressure changes and/or phase changes, such as vaporization of a liquid. The pressure and/or phase changes are needed for the oxygenate conversion process.

Light olefin products will form—although not necessarily in optimum amounts—at a wide range of pressures, including but not necessarily limited to sub- and super-atmospheric pressures and autogeneous pressures,—in the range of from about 1 kPa to about 100 MPa. A preferred pressure is in the range of from about 5 kPa to about 50 MPa, most preferably in the range of from about 50 kPa to about 500 kPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention.

A steady state or semi-steady state production of light olefin products may be attained and/or sustained over a period of time, largely determined by the reactor type, the reactor configuration, the temperature, the pressure, the catalyst selected, the amount of spent catalyst recirculated (if any), the level of catalyst regeneration, the amount of carbonaceous materials left on the regenerated or partially regenerated catalyst, the weight hourly space velocity (WHSV), the amount of quench medium used, and other relevant process design characteristics.

A wide range of WHSV, defined as weight of total oxygenate feedstock per hour per weight of catalyst, for the feed stock will function in the present invention. Depending on the reactor type, the desired conversion level, the feed stock composition, and other reaction parameters, the WHSV generally should be in the range of from about 0.01 $hr^{-1}$ to about 1000 $hr^{-1}$, preferably in the range of from about 0.1 $hr^{-1}$ to about 500 $hr^{-1}$, and most preferably in the range of from about 0.5 $hr^{-1}$ to about 200 $hr^{-1}$. Since the catalyst may contain other materials which act as inerts, fillers, or binders; the WHSV is calculated only on the weight basis of oxygenate and molecular sieve part of the catalyst.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other saturated hydrocarbons (such as methane, ethane, propane, and mixtures thereof), aromatic compounds, and mixtures thereof. Preferred diluents include, but are not necessarily limited to water and nitrogen.

Oxygenate conversion should be maintained sufficiently high to avoid the need for commercially unacceptable levels of recycling. 100% oxygenate conversion is preferred for the purpose of avoiding feedstock recycle completely. However, a reduction in unwanted by-products is observed frequently when the oxygenate, particularly methanol, conversion level is about 98% or less. Accordingly, there is usually from about 0.05 mol % to about 50 mol % unreacted oxygenate in the product stream along with the oxygenate conversion products comprising olefins, water, and/or other byproducts. It is preferable to recover as much of the unreacted oxygenate as possible for recycle purposes. In any event, the oxygenate content in waste water may need to be reduced to an environmentally acceptable level before byproduct water can be discharged.

Therefore, it is desirable to consider this incomplete oxygenate conversion in the overall heat recovery and heat integration scheme, i.e. optimizing heat recovery and heat integration, when using a fractionator to recover unreacted oxygenates. If the oxygenate conversion level is high enough and/or recovery of unreacted oxygenate is not warranted for economic or environmental purposes, then this invention calls for utilizing heat directly from the heavy product fraction or any or all of the several fractions into which the heavy product fraction may be divided.

After contacting the oxygenate feed, the catalyst becomes fully or partially deactivated due to accumulation of carbonaceous deposits (also called coke) on the catalyst surface and/or inside the pores. Fully deactivated catalyst The deactivated catalyst having carbonaceous deposits is separated from the other oxygenate conversion products. Preferably at least a portion of the deactivated catalyst is separated and withdrawn from the oxygenate conversion reactor intermittently, semi-continuously, continuously, or in batch. Before the deactivated catalyst is recycled back to the oxygenate conversion and used again, a suitable regeneration is carried out on at least a portion of the withdrawn deactivated catalyst to remove at least a portion of the carbonaceous deposits, in the range of from about 0.1 wt % to about 99.9 wt %, preferably at least about 1.0 wt % of the carbonaceous deposits should be removed. Complete regeneration—removing 100 wt % of the original carbonaceous deposits on all of the deactivated catalyst—also may be carried out, but it is found that complete regeneration has a tendency of leading to production of large amounts of undesirable byproducts such as methane and/or hydrogen.

Preferably, the regeneration is carried out in the presence of a gas comprising oxygen or other oxidants. Air and air diluted with nitrogen, steam, and/or $CO_2$ are preferred regeneration gases. The catalyst regeneration temperature should be in the range of from about 250° C. to about 750° C., preferably from about 300° C. to about 700° C.

Almost any type of reactor will provide some conversions of the oxygenates to olefins. Reactor type includes, but is not necessarily limited to fluidized bed reactor, riser reactor, moving bed reactor, fixed bed reactor, continuously stirred tank reactor, hybrids and combinations thereof. Increased heat recovery and improved heat integration in the present invention can be achieved with most any reactor types. A preferred reactor system for the present invention is a circulating fluid bed reactor with continuous or semi-continuous catalyst regeneration, similar to a modern fluid catalytic cracker. Fixed beds may be used, but are not preferred.

Because the oxygenate conversion reaction is highly exothermic, the oxygenate conversion reaction product effluent generally has a higher temperature than the feedstock temperature just before contacting the catalyst. In one embodiment of the present invention, the feedstock from the storage tank at a first temperature and having a first heat content is heated through several intermediate stages in heat exchangers to a second desired temperature prior to contacting the oxygenate conversion catalyst. It is preferable to have from one to about three stages of heat exchange to provide streams with successively higher heat contents. Various streams from the oxygenate conversion process at different temperatures and external sources of heat, such as that from steam, may be used as heat exchanger fluids to increase either the heat content, the temperature, or both, of the feedstock oxygenate.

After contacting the oxygenate feedstock with the oxygenate conversion catalyst, the oxygenate conversion reaction product effluent comprising olefin products is quenched directly by contacting a suitable quench medium in a quench tower without first going through a product fractionation step. Alternatively, the product effluent may be used to provide heat directly to the oxygenate feedstock. The temperature and the heat content of the product effluent are reduced to intermediate levels afterwards. The product effluent at this lower temperature and lower heat content is sent to the quench tower for direct quenching.

The compounds in the effluent stream which are gaseous under the quenching conditions are separated from the quench tower as a light product fraction for olefin product recovery and purification. The light product fraction comprises light olefins, dimethyl ether, methane, CO, $CO_2$, ethane, propane, and other minor components such as water and unreacted oxygenate feedstock. The compounds in the effluent stream which are liquid under quenching conditions, are separated from the quench tower as a heavy product fraction for heat recovery, and possible division into several fractions and separation of the quench medium. The heavy product fraction comprises byproduct water, a portion of the unreacted oxygenate feedstock (except those oxygenates that are gases under quenching conditions), a small portion of the oxygenate conversion byproducts, particularly heavy hydrocarbons (C5+), and usually the bulk of the quench medium.

Preferably, a quench medium is selected from a composition which remains substantially as a liquid under the quenching conditions, thus minimizing the amount of the quench medium present in the light gaseous product fraction which must undergo more expensive gaseous product processing steps to recover commercially acceptable grades of light olefin products. A preferred quench medium is selected from the group consisting of water and streams that are substantially water. More preferably, the quench medium is a stream which is substantially water and is selected from the several fractions of the heavy product fraction from the quench tower.

The amount of quench medium circulated in the quench tower at a particular temperature for product quenching should be not more than what is needed to produce a heavy product fraction exiting the quench tower having a temperature at least about 5° C. higher than the first temperature of the oxygenate feedstock from the storage tank. In another embodiment, as already discussed, the oxygenate conversion reactor effluent stream is used directly as a heat exchanger fluid to provide heat to the oxygenate feedstock before it enters the oxygenate conversion reactor to contact the oxygenate conversion catalyst.

Preferably, the pressure in the quench tower and the temperature of the heavy product fraction effluent are maintained at effective levels for recovery of the highest quantity and quality of process heat. More preferably, the difference between the heavy product fraction effluent pressure and the pressure at which the feedstock is vaporized is below about 345 kPa, more preferably below about 207 kPa. The temperature of the heavy product fraction effluent from the quench tower preferably is maintained at not less than about 30° C. below the bubble point of the heavy product fraction effluent. Maintaining a temperature differential between the heavy product fraction effluent and its bubble point provides the highest possible bottoms temperature in the quench tower and the most economically practical recovery of useful heat from the heavy product fraction effluent.

Preferably, the heavy product fraction effluent (heavy product fraction) from the quench tower is pressurized and used for providing heat to other streams. In one embodiment, the heavy product fraction, or any, or all of the several fractions into which the heavy product fraction is divided, or streams from quench medium separations thereof, are used directly as a heat exchanger fluid to increase the heat content and/or temperature of the oxygenate feedstock at one or more of the stages with successively higher heat contents. Further, any of the several fractions or streams produced from the quench medium separations thereof may be used to increase the heat contents of other streams within the overall oxygenate conversion reaction and product recovery process. The cooled quench medium recovered from such fractions and streams may be returned back to the quench tower.

In a preferred embodiment, particularly when the oxygenate conversion is not complete and the quench medium consists essentially of water, the heavy product fraction is divided into two fractions, a first fraction and a second fraction. The relative quantities of the first fraction and the second fraction depend on the overall amount of heat that needs to be removed from the product effluent stream in the quench operation, and the temperature of the quench medium introduced into the quench tower. The relative quantities are set to optimize equipment cost for heat recovery and utility consumptions. The first fraction is cooled to a desired temperature and sent back to the quench tower as a recycle, i.e. quench water. The utility required to cool the first fraction, e.g. cooling water, may be reduced by using the product effluent stream from the oxygenate conversion reactor as a heat exchange fluid to heat the oxygenate feedstock before the feedstock enters the oxygenate conversion reactor and/or before the product effluent stream enters the quench tower.

The second fraction of the heavy product fraction effluent is sent to a fractionator to separate the quench medium, which consists essentially of water—a part of it may originate as the recycled portion of the byproduct water from the oxygenate conversion reaction when the feedstock oxygenate has at least one oxygen—from other compounds, such as unreacted oxygenates or certain heavier hydrocarbons from the oxygenate conversion reaction, present in the fraction. If other streams having compositions similar to or compatible with the second fraction exist within the oxygenate conversion and the associated product recovery process, such other streams are combined with the second fraction first and the combined stream is sent to the fractionator.

Generally it is desirable to fractionate a mixture into components as sharply as possible. In the present invention, it is preferable for the overhead oxygenate fraction and/or the heavies-containing fraction from the fractionator to have a composition of water as introduced in the second fraction of the heavy product fraction in the range of from about 15 mol % to about 99.5 mol %, preferably from about 25 mol % to about 90 mol %. An increase in the water composition of the overhead fraction tends to increase the condensation temperature, and more heat can be recovered economically from the overhead fraction of the fractionator to improve heat integration for the entire process. Preferably, the recovered overhead oxygenate fraction contains at least about 90 mol % of the oxygenate contained in the second fraction of the heavy fraction. More preferably, the recovered overhead oxygenate fraction contains at least about 99 mol % of the oxygenate contained in the second fraction of the heavy fraction.

The overhead fraction of the fractionator is condensed in a heat exchanger, i.e. a condenser, against the oxygenate feedstock at one of the stages, from one to about three where the oxygenate feedstock is given successively higher heat contents. It s preferable for the overhead fraction of the fractionator to have a pressure at least about 69 kPa higher than the pressure of the oxygen feedstock in the condenser. This pressure differential also increases the condensation temperature of the overhead fraction, making heat recovery from the overhead fraction more economical.

The bottoms fraction of the fractionator consists essentially of byproduct water from the oxygenate conversion reaction. Preferably, this bottoms fraction is pressurized and used to heat the oxygenate feedstock at one of the stages, from one to about three, where the oxygenate feedstock is given successively higher heat contents prior to entering the oxygenate conversion reactor. The fractionator is operated such that the temperature of the bottoms fraction is at least about 5° C., preferably at least about 25° C., higher than the first temperature of the oxygenate feed from storage. The operating temperature inside of the fractionator is determined by a number of parameters, including, but not necessarily limited to the fractionator overhead pressure and the overall pressure drop inside of the fractionator.

Figure 1:
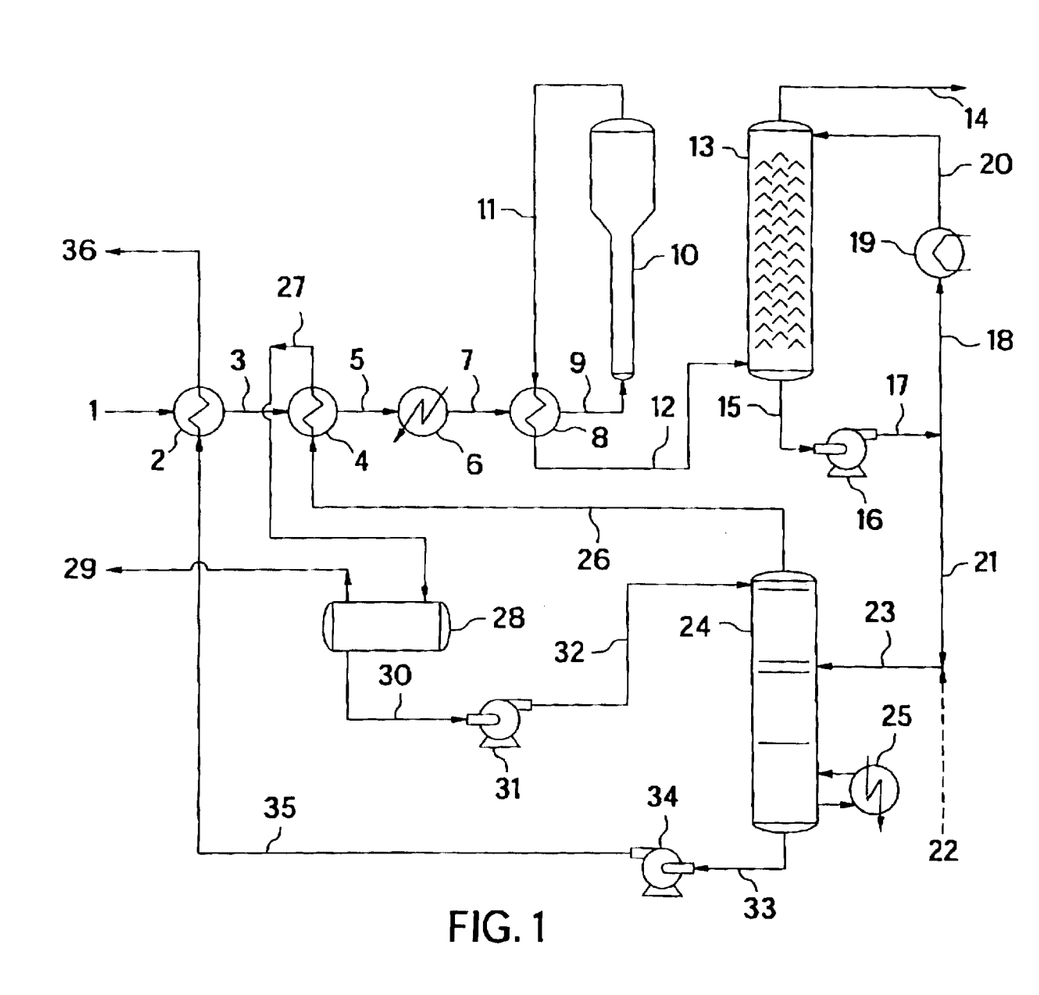
FIG. 1 is a flow diagram of a preferred embodiment of increasing heat recovery in the present invention.

FIG. 1 shows one embodiment of a process flow diagram according to the invention to increase heat recovery and to improve heat integration. Liquid oxygenate feed 1, such as methanol, having a first heat content, at a first temperature and a first pressure, is heated by stream 35 in heat exchanger 2. Stream 35 is fractionator bottoms stream 33 from fractionator 24, which is pressurized by pump 34. The result is a first heated oxygenate feed stream 3 with a higher heat content than that of liquid oxygenate feed stream 1. First heated oxygenate feed stream 3 then is heated in another heat exchanger 4 by overhead fraction 26 from fractionator 24 to form a second heated oxygenate feed stream 5 with a higher heat content than that of stream 3. Heat exchanger 4 is a condenser or a partial condenser for fractionator 24. Second heated oxygenate feed stream 5 goes through steam pre-heater 6 to form a third heated oxygenate feed stream 7 which is further heated by oxygenate conversion product effluent 11 in heat exchanger 8 to form a fourth heated oxygenate feed stream 9 under the effective conditions—temperature, pressure, and proportion of liquid and vapor—desired for the conversion of the oxygenate feed. Oxygenate conversion product 11 is the effluent of oxygenate conversion reactor 10, after being separated from the deactivated oxygenate conversion catalyst which has carbonaceous deposits. Alternatively, heat exchanger 8 may comprise of a plurality of coils inside of oxygenate conversion reactor 10.

Fourth heated oxygenate feed stream 9 is fed to oxygenate conversion reactor 10 which contains catalyst suitable for converting the oxygenate feed to olefins. Oxygenate conversion reactor 10 may adopt various configurations—fixed bed, fluidized bed, riser, moving bed, or a combination thereof, with or without continuous catalyst regeneration. A fixed bed reactor normally is not favored due to the difficulty of withdrawing deactivated catalyst for regeneration and returning the regenerated catalyst back to the reactor. The oxygenate feed is converted to a product comprising light olefins and the catalyst becomes deactivated or partially deactivated by accumulating carbonaceous deposits which are formed as byproducts of the oxygenate conversion reaction.

Oxygenate conversion product effluent 11 flows through heat exchanger 8 and becomes cooled oxygenate conversion product effluent stream 12 which is sent to quench tower 13. Alternately, heat exchanger 8 may be eliminated and oxygenate conversion product effluent 11 is sent directly to quench tower 13 without intermediate cooling. In quench tower 13 oxygenate conversion product stream 12 contacts directly with a quench medium consisting essentially of water at an initial temperature over a series of suitable contacting devices. The amount of the quench medium needed in quench tower 13 is dictated by a number of factors, including, but not necessarily limited to the composition of the quench medium, the temperature of quench medium recycle introduced to quench tower 13, and desired temperature differences and pressure differences between various streams. These differences are discussed where appropriate. The gaseous products are separated as light product fraction stream 14. Heavy product fraction stream 15, which exits from the bottom of the quench tower at an exiting temperature, comprises the bulk of byproduct water, a portion of the unreacted oxygenate feedstock (except those oxygenates that are gaseous under the quenching conditions), a small portion of the oxygenate conversion byproducts, particularly heavy hydrocarbons (C5+), and usually the bulk of the quench medium.

A preferred quench medium is water, which is for all intents and purposes indistinguishable from byproduct water. This eliminates the need for steps to separate the quench medium from byproduct water in the heavy product fraction. In the event that a quench material other than water is used and this quench material is substantially in a liquid form under quenching conditions, heavy product fraction 15, or any, or all of the several fraction into which the heavy product fraction is divided may be processed to separate the quench medium from byproduct water. For example, if the quench medium is a high boiling hydrocarbon such as diesel fuel or similar streams, it is immiscible with byproduct water. Such a quench medium can be separated by a properly designed weir system in the bottom of quench tower 13, or in an API separator or other similar devices at many different points of the process in the present invention. Further, if any heavy hydrocarbons (C5+) are formed in the oxygenate conversion reaction, they also may be removed from byproduct water in stream 15 or other points in the process in substantially the same manner as or along with the removal of the quench medium. If the quench medium is a relatively light material which is substantially gaseous under the quenching conditions, and hence being present in substantial quantities in the light product fraction, such a quench medium can be separated in downstream olefin recovery processes encompassing the entire oxygenate conversion and olefin recovery and purification process.

Regardless, the exiting pressure of heavy product fraction stream 15 should be less than about $345 \times 10^3$ pascals (345 kPa) below the pressure of liquid oxygenate feed 1. Preferably, the exiting temperature of heavy product fraction stream 15 is maintained at not less than about 25° C. below the bubble point of byproduct water in stream 15. A preferred pressure difference between heavy product fraction stream 15 (lower pressure) and liquid oxygenate feed 1 (higher pressure) is less than 207 kPa.

Heavy product fraction stream (quench tower bottoms stream) 15 may be used to provide heat to the oxygenate feedstock in heat exchangers 2, 4, and/or 6 to increase the heat content of the feedstock. The oxygenate feedstock contains successively higher heat contents at these stages. One or more of these stages also may be eliminated. Preferably, quench tower bottoms stream 15 is divided into to two fractions, recycle fraction 18 and fractionator feed fraction 21. Recycle fraction 18, a quench water recycle stream, is cooled in exchanger 19 and recycled as quenching stream 20 back to quench tower 13. Alternatively, recycle fraction 18 or 20 may be split further into several fractions and these fractions may be cooled to different temperatures in different heat exchangers. These fractions, or some of them, at different temperatures may be introduced into quench tower 13 at different points to better integrate heat recovery and minimize utility consumption. The heat content of fraction 18 may be used to provide heat to the oxygenate feedstock in the heat exchanger 2, 4, and/or 6, or at different locations of the entire oxygenate conversion and olefin recovery and purification process to provide heat and to increase heat recovery.

Fractionator feed fraction 21, optionally mixed with other water containing streams 22, is sent to fractionator 24. At least two streams, fractionator overhead stream 26 and fractionator bottoms stream 33, are fractionated from fractionator feed fraction 21. Fractionator overhead stream 26 should contain at least about 15 mol %, preferably at least about 25 mol %, of water from the oxygenate conversion reaction. Conjunctively with or alternatively to this composition preference, the temperature of fractionator overhead stream 26 should be at least about 10° C. higher than the boiling temperature of the oxygenate feed under the conditions of heat exchanger 4.

Sufficient heat is added to fractionator 24 via reboiler 25, which when coupled with a sufficient number of trays in fractionator 24 results in producing fractionator bottoms stream 33 which comprises substantially all byproduct water and quench medium introduced with stream 23.

Preferably, the quench medium is water. When water is used as the quench medium, bottoms stream 33 consists essentially of the bulk of byproduct water from the oxygenate conversion reaction and no further steps are necessary to separate byproduct water from the quench medium. If the quench medium is a material other than water and has not previously been separated from byproduct water prior to introduction into the quench tower, this quench material may be separated from byproduct water in bottoms stream 33, or later in the process as described above. Further, if any heavy hydrocarbons (C5+) are formed in the oxygenate conversion process, they also may be removed from byproduct water in stream 33, or later in the process in substantially the same manner as or along with the removal of the quench medium.

Fractionator bottoms stream 33, before leaving fractionator 24, is at a temperature which is at least about 5° C., preferably at least about 25° C., higher than the first temperature of the oxygenate feed introduced from storage 1 to heat exchanger 2. The pressure at the top of fractionator 24 should be at least 69 kPa higher than the pressure in heat exchanger 4 to increase heat recovery. Stream 35 is used to heat up liquid oxygenate feedstock 1 in heat exchanger 2. For better heat recovery, exiting stream 36 from heat exchanger 2 preferably has a temperature equal to or less than about the temperature of stream 21.

One way to further improve heat integration and to increase heat recovery is to use fractionator overhead stream 26 as the heat source for heat exchanger 4. The cooled fractionator overhead stream 27 may be fractionated further in separator 28 into vapor discharge stream 29 and liquid reflux 30 which is sent back to fractionator 24 after pressure adjustment with pump 31. It is important to maintain cooled fractionator overhead stream 27 at a temperature above the boiling point of the first heated oxygenate feed 3 to provide favorable heat transfer.

Another embodiment of this invention relates to converting oxygenates to olefins with high energy and capital efficiency. In this preferred embodiment, an indirect heat transfer device for transferring heat from at least a portion of an effluent of an oxygenate conversion reactor to the feedstock is used to cause at least a portion of the feedstock to vaporize. For example, in FIG. 1, the indirect heat transfer device would be heat exchanger 8 and the effluent of the oxygenate conversion reactor is stream 10. In a preferred embodiment, the heat transfer device is a thermosiphon utilizing a disengaging or circulation drum.

As defined herein, the boiling range of a feedstock is the difference in the temperature of that feedstock at its dew-point and its bubble point at any one pressure of operation of the feedstock within the heat transfer device. If the feedstock is a single component feedstock, e.g., a substantially pure methanol, the feedstock has a single temperature boiling point at any one pressure. Thus it has a 0° C. boiling range. Typically, the feedstock will comprise one or more components having different boiling points, e.g., methanol, diluents, and other hydrocarbon components. Typically, the feedstock will have more than one component, and have a boiling point range of at least 2° C.

In a preferred embodiment, the boiling range is not greater than about 30° C., 25° C., 20° C., 15° C., 10° C. and most preferably not greater than about 5 to 6° C. The oxygenate conversion reactor converts at least a portion of the feedstock into the effluent, and the effluent comprises the olefins.

Desirably, the temperature of the reactor effluent is at least 300° C., more preferably at least 350° C., and most preferably at least 400° C. The temperature of the reactor effluent preferably is below about 700° C. to achieve attractive yields in the oxygenate conversion reaction.

In another embodiment, a portion of the heat in the reactor effluent emanating from the indirect heat transfer device vaporizing the feedstock is used to increase the sensible heat of the feedstock prior to vaporization of the feedstock. This heat is particularly useful for adding sensible heat (which is increasing the heat content to a liquid without vaporizing it, so the feedstock must be below its bubble point) to the feedstock.

In another embodiment, the sensible heat is provided in a separate indirect heat transfer device from that used for vaporization. Preferably, the sensible heat is added to the feedstock in a separate indirect heat transfer device prior to introducing it to the vaporization indirect heat transfer device.

In another embodiment, the reactor effluent provides heat of vaporization, or increase in sensible heat, to more than one feed stock in separate indirect heat transfer devices. The indirect heat transfer devices that can be used to transfer heat include, for example, tubular exchangers, fin-type exchangers, condensers, scraped-surface exchangers, agitated vessels and thermosiphon-boilers. A thermosiphon-boiler is a device wherein natural circulation of the boiling medium is obtained by maintaining sufficient liquid head to provide for circulation, i.e., circulation of feedstock through the device occurs by density differences and is not forced by pumps. A separate vessel, desirably a drum in fluid communication with the exchanger, can be used to receive the partially vaporized feedstock exiting the exchanger, separate the liquid and vapor, and return the liquid to the entrance of the exchanger. Fresh liquid or partially liquid feedstock can also be sent to the seperate vessel, rather than directly to the heat exchanger.

The thermosiphon-boiler is a particularly useful embodiment for vaporization of feedstock. Tubular exchangers include a shell-and-tube-type heat exchanger, a U-tube heat exchanger, a packed-lantern-ring exchanger, a outside-packed floating-head exchanger, an internal floating-head exchanger, a bent-tube fixed-tube-sheet exchanger, a bayonet-tube exchanger, a spiral-tube exchanger, a falling-film exchanger and Teflon-head exchanger.

The temperature of cooled reactor effluent is preferably not less than 30° C. below the water dewpoint. In the method of this invention, determining the boiling range of a feedstock and the water dewpoint of a cooled reactor effluent, and many other useful thermodynamic properties of the materials utilized, is desireably determined by the Soave Modified Redlich-Kwong (SMRK) equation of state. The SMRK equation is readily available in SimSci PRO/II, which is a computer program for chemical process simulation.

In another embodiment, the reactor effluent stream can be split, using one part to vaporize feedstock in one device. Other parts may be used to provide heat to other materials in other devices. In a preferred embodiment, one part of the reactor effluent may be used to vaporize oxygenate and another part may be used to vaporize diluent (or a mix of diluent and oxygenate) in another device, in a parallel approach, feeding both streams to the reactor. In another embodiment, all or part of the reactor effluent may be used to in one device to vaporize diluent, then the reactor effluent from that device is sent to another device to vaporize oxygenate (or a mix of diluent and oxygenate), or the order of vaporization may be reversed, in a series approach. The best approach will be determined based upon the selection of oxygenate and diluent employed, and other economic and process criteria, such as desired energy efficiency and capital return requirements, using engineering design and economic principles well known to those skilled in the art and not discussed in detail here.

In other embodiments, the diluent can have a normal boiling point between −20° C. and 130° C.; preferably −6° C. and 100° C.; and most preferably 35° C. and 90° C. The diluent is desirably an aliphatic and aromatic hydrocarbons; $C_4$ to $C_8$ aliphatic and olefinic hydrocarbons and $C_6$–$C_8$ aromatics. Most preferably, the diluent is iso- or normal hexane.

It is particularly beneficial for the diluent to have a relatively low normal boiling point, i.e., bubble point at one atmosphere pressure, to allow it to be vaporized at a temperature under the operating conditions of the vaporizer that is low enough to provide high temperature differentials with the reactor effluent. It should not, however, be so low that it cannot remain a liquid at the operating pressures of vaporizer and reactor. Especially useful is when the diluent has a normal boiling point close to that of the oxygenate feed, so that it can be mixed with the oxygenate in large proportion, if desired, and still maintain a low boiling range. This may make it possible to perform as much of the heating of the feedstock, both sensible heat and vaporization of both oxygenate and diluent, in as few exchangers as possible.

The preferred diluents have desirable boiling ranges and normal boiling points. An added attractive feature is they have relatively low heats of vaporization (compared to oxygenates and water/steam). This would allow the heat from the reactor effluent to be most effectively utilized in vaporizing the feedstock sent to the reactor, particularly that fraction which may be obtained in condensing the water out of the reactor effluent, if so chosen. Iso- and normal hexane are particularly useful diluents when the oxygenate is methanol.

The process can be operated with a feedstock in which 0.1–100% of the feedstock is in a liquid state. In other variations, the feedstock could be at least 10%, 20%, 30%, 40%, 50%, 60%, 70%, 80% and 90% in a liquid state. Preferably, the temperature of the feedstock is not less than 30° C. lower than its bubble point at the location, and hence at the pressure, it is introduced to the heat exchange device in which it will be vaporized, more preferably not less than 20° C. lower, still more preferably not less than 10° C. lower, and most desirably no more than 6° C. lower.

The invention will be better understood with reference to the following example, which illustrate, but should not be construed as limiting the present invention.

EXAMPLE I

A liquid methanol feed 1 at about 386.1 kPa pressure and 38° C. absorbs heat to increase its heat content in heat exchanger 2 from stream 35, at 158° C. and 1,276 kPa pressure, from methanol/water fractionator 24 to form the first heated methanol feed stream 3 at a temperature of about 100° C. and a pressure of 351.6 kPa. The first heated methanol feed stream 3 with 4,722 kJ/mole heat content absorbs heat from the fractionator overhead stream 26 in the heat exchanger 4 to form the second heated methanol feed stream 5 with a heat content of 6,521 kJ/mole. Stream 5 is heated further by steam in heat exchanger 6 to form the third heated methanol feed stream 7 which has even higher heat content than the third heated methanol feed stream 7—7,390 kJ/mole. The third heated methanol feed stream 7 is heated in heat exchanger 8 to form the fourth heated methanol feed stream 9 with the methanol conversion product effluent 11 from the oxygenate conversion reactor 10. The fourth heated methanol feed stream 9, having a much higher heat content of 17,102 kJ/mole, is suitable for contacting a catalyst in the oxygenate conversion reactor 10 to form a deactivated oxygenate conversion catalyst having carbonaceous deposits and a product 11 comprising olefins, particularly light olefins. The oxygenate conversion reactor 10 is a fluidized bed reactor with continuous catalyst regeneration and recirculation (not shown). The oxygenate conversion product 11 is separated from deactivated oxygenate conversion catalyst having carbonaceous deposits and used to heat the stream 9 and form a cooled methanol conversion product stream 12. A part of the deactivated catalyst is withdrawn and removed for regeneration. (not shown). It is preferable to remove at least about 1.0 wt % of the carbonaceous deposits from the deactivated catalyst during the regeneration. It is also preferred to remove less than about 98.0 wt % of the carbonaceous deposits from the deactivated catalyst during regeneration. The regenerated catalyst is recycled back into the oxygenate conversion reactor 10 for contacting the oxygenate feed. 99.8 wt % of the methanol in stream 9 is converted in the reactor 10, with the unconverted balance exiting in the stream 11.

The cooled methanol conversion product stream 12 exiting the heat exchanger 8 is sent to the quench tower 13, contacting directly a quench medium consisting essentially of water. The quench tower 13 is equipped with suitable contacting devices inside. Most hydrocarbon products are separated as a gaseous product stream 14. Heavier products, water, and unreacted methanol are discharge from the quench tower 13 as the quench tower bottoms stream 15 at a temperature of about 116° C. and a pressure of about 262 kPa. The quench tower bottoms stream 15 is pressurized by the pump 16 to form the pressurized quench tower bottoms stream 17 at about 689.5 kPa. About 83 mol % of the pressurized quench tower bottoms stream 17 forms the recycle fraction 18 and is sent through the cooling exchanger 19 to form the quenching stream 20 at a lower temperature. The quenching stream 20 is returned to the quench tower 13.

The rest of the pressurized quench tower bottoms stream 17, about 17 mol % becomes the fractionator feed fraction 21. The fractionator feed fraction 21 is combined with another methanol/water stream 22, a small stream recovered from other sources within the overall oxygenate conversion and product recovery process. The combined stream 23 is sent to the fractionator 24. The fractionator overhead stream 26 containing about 89 mol % water and about 10.5 mol % of methanol at a temperature of 152° C. and a pressure at 551.6 kPa is sent to the heat exchanger 4. The bottoms from fractionator 24 is heated with steam in the heat exchanger 25 to produce the fractionator bottoms stream 33 at 158° C. and about 585.4 kPa, which contains primarily water with only traces of other components. The fractionator bottoms stream 33 is pressurized to about 1274.8 kPa and the resulting stream 35 is used for the heat exchanger 2 to heat the liquid methanol feed 1. After heat exchange, the byproduct warm water stream 36 has a temperature of 46° C. at a pressure of 861.2 kPa.

Table 1 shows the product selectivity and the composition of product stream 11 of methanol conversion used for obtaining the results shown in Table 2 and Table 3. The feed rates, compositions, pressures, and temperatures of various streams as described in Example I are shown in Table 2. The duties of key exchangers 2, 4, and 25 are tabulated in Table 3. Tables 2 and 3 were compiled using the Simulation Sciences, Inc. PRO/II chemical process simulation program, utilizing the Modified Panagiotopoulos-Reid modifications to the Soave-edlich-Kwong equation of state.

TABLE 1

| Component | Product Selectivity (wt %) | Hydrocarbon Composition in Stream 11 (mol %) |
|---|---|---|
| Hydrogen | 0.15 | 0.73 |
| Carbon Monoxide | 0.03 | 0.01 |
| Carbon Dioxide | 0.12 | 0.03 |
| Methane | 1.00 | 0.61 |

TABLE 1-continued

| Component | Product Selectivity (wt %) | Hydrocarbon Composition in Stream 11 (mol %) |
|---|---|---|
| Ethylene | 40.90 | 14.40 |
| Ethane | 0.83 | 0.27 |
| Propylene | 40.90 | 9.60 |
| Propane | 0.21 | 0.05 |
| Butenes | 8.89 | 1.56 |
| Butanes | 0.09 | 0.02 |
| Pentenes | 3.95 | 0.56 |
| Pentanes | 0.04 | 0.01 |
| Coke | 2.89 | — |
| Total | 100.00 | 27.84 |

TABLE 2

| Stream No. | Rate (mol/h) | Methanol (mol %) | Water (mol %) | Pressure (kPa) | Temperature (° C.) | Heat Content (kJ/mol) |
|---|---|---|---|---|---|---|
| 1 | 10,000.0 | 98.23 | 1.77 | 386.1 | 35.2 | 582 |
| 3 | 10,000.0 | 98.23 | 1.77 | 351.6 | 100.1 | 4,722 |
| 5 | 10,000.0 | 98.23 | 1.77 | 330.9 | 98.2 | 6,521 |
| 7 | 10,000.0 | 98.23 | 1.77 | 317.2 | 96.9 | 7,390 |
| 9 | 10,000.0 | 98.23 | 1.77 | 317.2 | 96.9 | 17,102 |
| 11 | 13,918.9 | 0.14 | 72.02 | 275.8 | 407.9 | 25,424 |
| 12 | 13,918.9 | 0.14 | 72.02 | 262.0 | 124.9 | 18,475 |
| 14 | 3,946.7 | 0.04 | 1.78 | 241.3 | 37.8 | 6,841 |
| 15 | 92,909.4 | 0.18 | 99.82 | 262.0 | 115.6 | 3,856 |
| 21 | 9,972.2 | 0.18 | 99.82 | 689.5 | 115.6 | 3,859 |
| 22 | 863.8 | 0.21 | 99.78 | 689.5 | 43.4 | 1,394 |
| 26 | 1,118.0 | 10.54 | 89.42 | 551.6 | 151.9 | 21,740 |
| 27 | 1,118.0 | 10.54 | 89.42 | 517.1 | 138.8 | 5,566 |
| 29 | 53.9 | 36.42 | 62.75 | 517.1 | 138.8 | 886 |
| 33 | 10,782.2 | trace | 100.00 | 585.4 | 157.9 | 5,302 |
| 35 | 10,782.2 | trace | 100.00 | 1,274.8 | 158.1 | 5,310 |
| 36 | 10,782.2 | trace | 100.00 | 861.2 | 46.1 | 1,476 |

TABLE 3

| Exchanger No. | Duty ($10^6$ kJ/h) |
|---|---|
| 2 | 41.4 |
| 4 | 18.9 |
| 6 | 8.6 |
| 8 | 97.1 |
| 19 | 191.7 |
| 25 | 38.1 |

These results show that in the oxygenate conversion process, the external heat needed to bring the oxygenate feedstock to conditions desirable for contacting the catalyst, represented in the preferred embodiment by heat exchanger 6, is reduced as a result of increased heat recovery and improved heat integration of the process.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

We claim:

1. A process for converting an oxygenate to olefins, the process comprising:
providing a feedstock having more than one component including the oxygenate,
heating the feedstock from a first temperature to a second temperature,
converting at least a portion of the oxygenate in the heated feedstock into an olefin-containing effluent in an oxygenate conversion reactor, and
quenching the effluent with a medium at an initial temperature and in an amount sufficient for forming a light product fraction and a heavy product fraction wherein the light product fraction comprises light olefins and the heavy product fraction has a final temperature which is higher than the first temperature by at least about 5° C.,
wherein the heating includes transferring heat from at least a portion of the heavy product fraction to the feedstock to cause at least a portion of the feedstock to vaporize and form a vaporized feedstock, and wherein the feedstock has a boiling range ranging from 2° C. to about 30° C.

2. The process of claim 1, wherein the feedstock further comprises a diluent.

3. The process of claim 1, wherein the feedstock is selected from the group consisting of an impure methanol having a boiling range and a mixture of methanol and dimethyl ether.

4. The process of claim 1, wherein the oxygenate is selected from the group consisting of methanol, dimethyl ether, ethanol, methyl ethyl ether, dimethyl carbonate, methyl formate, methyl acetate, diethyl ether, and mixtures thereof.

5. The process of claim 1, wherein the catalyst is selected from the group consisting of a zeolite, a silicoaluminophosphate (SAPO), a substituted silicoalumino-phosphate, a substituted aluminophosphate and mixtures thereof.

6. The process of claim 5, wherein the catalyst is a SAPO selected from the group consisting of SAPO-17, SAPO-18, SAPO-34, SAPO-44, and mixtures thereof.

7. The process of claim 2, wherein the diluent is a hydrocarbon selected from the group consisting of C4 to C8 olefin, C4 to C8 aliphatic, C6–C8 aromatic and mixtures thereof.

8. The process of claim 2, wherein the diluent is a hydrocarbon selected from the group consisting of iso- and normal hexane and mixtures thereof.

9. The process of claim 2, wherein the diluent has a normal boiling point of about 35° C. to about 90° C.

10. The process of claim 1, wherein the boiling range is no greater than about 20° C.

11. The process of claim 1, wherein the boiling range is no greater than about 10° C.

12. The process of claim 1, wherein the final temperature is at least about 350° C.

13. The process of claim 1, wherein 0.1–100% of the feedstock is in a liquid state.

14. The process of claim 1, wherein at least about 80% of the feedstock is in a liquid state.

15. The process of claim 1, wherein at least about 20% of the feedstock is in a liquid state.

16. The process of claim 1, wherein a temperature of the feedstock is not less than 30° C. lower than the bubble point of the feedstock at a location where the feedstock is introduced to a heat transfer device that transfers heat from the heavy product fraction to the feedstock.

17. The process of claim 1, wherein at least a portion of the heat transferred from the heavy product fraction to the feedstock provides sensible heat.

18. The process of claim 1, wherein a temperature of the heavy product fraction after transferring heat to the feedstock is not less than 30° C. below water dewpoint.

19. The process of claim 1, wherein the heat transferred from the heavy product fraction to the feedstock is done in an indirect heat transfer device.

20. The process of claim 19, wherein the indirect heat transfer device is selected from the group consisting of a shell-and-tube-type exchanger and a thermosiphon-boiler.

21. A process for converting an oxygenate to olefins, the process comprising:
providing a feedstock having more than one component including the oxygenate,
heating the feedstock from a first temperature to a second temperature,
converting at least a portion of the oxygenate in the heated feedstock into an olefin-containing effluent in an oxygenate conversion reactor, and
quenching the effluent with a medium at an initial temperature and in an amount sufficient for forming a light product fraction and a heavy product fraction wherein the light product fraction comprises light olefins and the heavy product fraction has a final temperature which is higher than the first temperature by at least about 5° C.,
wherein the heating includes transferring heat from at least a portion of the heavy product fraction to the feedstock to cause at least a portion of the feedstock to vaporize and form a vaporized feedstock, and
wherein the converting comprises contacting the vaporized feedstock at a temperature from about 200 to about 750° C. and a pressure from 1 kPa to 100 MPa with a catalyst comprising a molecular sieve having a pore diameter smaller than 10 Angstroms, and wherein the feedstock has a boiling range ranging from 2° C. to about 30° C.

22. The process of claim 21, wherein the feedstock further comprises a diluent.

23. The process of claim 21, wherein the feedstock is selected from the group consisting of an impure methanol having a boiling range and a mixture of methanol and dimethyl ether.

24. The process of claim 21, wherein the oxygenate is selected from the group consisting of methanol, dimethyl ether, ethanol, methyl ethyl ether, dimethyl carbonate, methyl formate, methyl acetate, diethyl ether, and mixtures thereof.

25. The process of claim 21, wherein the catalyst is selected from the group consisting of a zeolite, a silicoaluminophosphate (SAPO), a substituted silicoaluminophosphate, a substituted aluminophosphate and mixtures thereof.

26. The process of claim 25, wherein the catalyst is a SAPO selected from the group consisting of SAPO-17, SAPO-18, SAPO-34, SAPO-44, and mixtures thereof.

27. The process of claim 22, wherein the diluent is a hydrocarbon selected from the group consisting of C4 to C8 olefin, C4 to C8 aliphatic, C6–C8 aromatic and mixtures thereof.

28. The process of claim 22, wherein the diluent is a hydrocarbon selected from the group consisting of iso- and normal hexane and mixtures thereof.

29. The process of claim 22, wherein the diluent has a normal boiling point of about 35° C. to about 90° C.

30. The process of claim 21, wherein the boiling range is no greater than about 20° C.

31. The process of claim 21, wherein the boiling range is no greater than about 10° C.

32. The process of claim 21, wherein the final temperature is at least about 350° C.

33. The process of claim 21, wherein 0.1–100% of the feedstock is in a liquid state.

34. The process of claim 21, wherein at least about 80% of the feedstock is in a liquid state.

35. The process of claim 21, wherein at least about 20% of the feedstock is in a liquid state.

36. The process of claim 21, wherein a temperature of the feedstock is not less than 30° C. lower than the bubble point of the feedstock at a location where the feedstock is introduced to a heat transfer device that transfers heat from the heavy product fraction to the feedstock.

37. The process of claim 21, wherein at least a portion of the heat transferred from the heavy product fraction to the feedstock provides sensible heat.

38. The process of claim 21, wherein a temperature of the heavy product fraction after transferring heat to the feedstock is not less than 30° C. below water dewpoint.

39. The process of claim 21, wherein the heat transferred from the heavy product fraction to the feedstock is done in an indirect heat transfer device.

40. The process of claim 39, wherein the indirect heat transfer device is selected from the group consisting of a shell-and-tube-type exchanger and a thermosiphon-boiler.

41. A process for converting an oxygenate to olefins, the process comprising:
providing a feedstock comprising the oxygenate and a diluent,
heating the feedstock from a first temperature to a second temperature,
converting at least a portion of the oxygenate in the heated feedstock into an olefin-containing effluent in an oxygenate conversion reactor,
quenching the effluent with a medium at an initial temperature and in an amount sufficient for forming a light product fraction and a heavy product fraction wherein the light product fraction comprises light olefins and the heavy product fraction has a final temperature which is higher than the first temperature by at least about 5° C.,
wherein the heating includes transferring heat from at least a portion of the heavy product fraction to the feedstock to cause at least a portion of the feedstock to vaporize and form a vaporized feedstock, and
separating the diluent from said effluent,
wherein the feedstock has a boiling range ranging from 2° C. to about 30° C.

42. The process of claim 41, wherein the feedstock is selected from the group consisting of an impure methanol having a boiling range and a mixture of methanol and dimethyl ether.

43. The process of claim 41, wherein the oxygenate is selected from the group consisting of methanol, dimethyl ether, ethanol, methyl ethyl ether, dimethyl carbonate, methyl formate, methyl acetate, diethyl ether, and mixtures thereof.

44. The process of claim 41, wherein the catalyst is selected from the group consisting of a zeolite, a silicoaluminophosphate (SAPO), a substituted silicoaluminophosphate, a substituted aluminophosphate and mixtures thereof.

45. The process of claim 44, wherein the catalyst is a SAPO selected from the group consisting of SAPO-17, SAPO-18, SAPO-34, SAPO-44, and mixtures thereof.

46. The process of claim 41, wherein the diluent is a hydrocarbon selected from the group consisting of C4 to C8 olefin, C4 to C8 aliphatic, C6–C8 aromatic and mixtures thereof.

47. The process of claim 41, wherein the diluent is a hydrocarbon selected from the group consisting of iso- and normal hexane and mixtures thereof.

48. The process of claim 41, wherein the diluent has a normal boiling point of about 35° C. to about 90° C.

49. The process of claim 41, wherein the boiling range is no greater than about 20° C.

50. The process of claim 41, wherein the boiling range is no greater than about 10° C.

51. The process of claim 41, wherein the final temperature is at least about 350° C.

52. The process of claim 41, wherein a temperature of the heavy product fraction before transferring heat from the effluent to the feedstock is at least about 300° C.

53. The process of claim 41, wherein 0.1–100% of the feedstock is in a liquid state.

54. The process of claim 41, wherein at least about 80% of the feedstock is in a liquid state.

55. The process of claim 41, wherein at least about 20% of the feedstock is in a liquid state.

56. The process of claim 41, wherein a temperature of the feedstock is not less than 30° C. lower than the bubble point of the feedstock at a location where the feedstock is introduced to a heat transfer device that transfers heat from the heavy product fraction to the feedstock.

57. The process of claim 41, wherein at least a portion of the heat transferred from the heavy product fraction to the feedstock provides sensible heat.

58. The process of claim 41, wherein a temperature of the heavy product fraction after transferring heat to the feedstock is not less than 30° C. below water dewpoint.

59. The process of claim 41, wherein the heat transferred from the heavy product fraction to the feedstock is done in an indirect heat transfer device.

60. The process of claim 59, wherein the indirect heat transfer device is selected from the group consisting of a shell-and-tube-type exchanger and a thermosiphon-boiler.

61. A process for converting an oxygenate to olefins, the process comprising:

providing a feedstock comprising the oxygenate and a diluent, heating the feedstock from a first temperature to a second temperature, converting at least a portion of the oxygenate in the heated feedstock into an olefin-containing effluent in an oxygenate conversion reactor, quenching the effluent with a medium at an initial temperature and in an amount sufficient for forming a light product fraction and a heavy product faction wherein the light product fraction comprises light olefins and the heavy product fraction has a final temperature which is higher than the first temperature by at least about 5° C., wherein the heating includes transferring heat from at least a portion of the heavy product fraction to the feedstock to cause at least a portion of the feedstock to vaporize and form a vaporized feedstock, and separating the diluent from said effluent, wherein the converting comprises contacting the vaporized feedstock at a temperature from about 200 to about 750° C. and a pressure from 1 kPa to 100 Mpa with a catalyst comprising a molecular sieve having a pore diameter smaller than 10 Angstroms and wherein the feedstock has a boiling range ranging from about 2° C. to about 30° C.

62. The process of claim 61, wherein the feedstock is selected from the group consisting of an impure methanol having a boiling range and a mixture of methanol and dimethyl ether.

63. The process of claim 61, wherein the oxygenate is selected from the group consisting of methanol, dimethyl ether, ethanol, methyl ethyl ether, dimethyl carbonate, methyl formate, methyl acetate, diethyl ether, and mixtures thereof.

64. The process of claim 61, wherein the catalyst is selected from the group consisting of a zeolite, a silicoaluminophosphate (SAPO), a substituted silicoaluminophosphate, a substituted aluminophosphate and mixtures thereof.

65. The process of claim 64, wherein the catalyst is a SAPO selected from the group consisting of SAPO-17, SAPO-18, SAPO-34, SAPO-44, and mixtures thereof.

66. The process of claim 61, wherein the diluent is a hydrocarbon selected from the group consisting of C4 to C8 olefin, C4 to C8 aliphatic, C6–C8 aromatic and mixtures thereof.

67. The process of claim 61, wherein the diluent is a hydrocarbon selected from the group consisting of iso- and normal hexane and mixtures thereof.

68. The process of claim 61, wherein the diluent has a normal boiling point of about 35° C. to about 90° C.

69. The process of claim 61, wherein the boiling range is no greater than about 20° C.

70. The process of claim 61, wherein the boiling range is no greater than about 10° C.

71. The process of claim 61, wherein the final temperature is at least about 350° C.

72. The process of claim 61, wherein the final temperature is at least about 300° C.

73. The process of claim 61, wherein 0.1–100% of the feedstock is in a liquid state.

74. The process of claim 61, wherein at least about 80% of the feedstock is in a liquid state.

75. The process of claim 61, wherein at least about 20% of the feedstock is in a liquid state.

76. The process of claim 61, wherein a temperature of the feedstock is not less than 30° C. lower than the bubble point of the feedstock at a location where the feedstock is introduced to a heat transfer device that transfers heat from the heavy product fraction to the feedstock.

77. The process of claim 61, wherein at least a portion of the heat transferred from the heavy product fraction to the feedstock provides sensible heat.

78. The process of claim 61, wherein a temperature of the heavy product fraction after transferring heat to the feedstock is not less than 30° C. below water dewpoint as determined by the Soave Modified Redlich-Kwong equation of state.

79. The process of claim 61, wherein the heat transferred from the heavy product fraction to the feedstock is done in an indirect heat transfer device.

80. The process of claim 79, wherein the indirect heat transfer device is selected from the group consisting of a shell-and-tube-type exchanger and a thermosiphon-boiler.

81. The method of claim 1, further comprising:

directing at least a portion of the effluent to a fractionator, and transferring heat from at least a portion of the effluent from the fractionator to the feedstock.

82. The method of claim 21, further comprising:

directing at least a portion of the effluent to a fractionator, and transferring heat from at least a portion of the effluent from the fractionator to the feedstock.

83. The method of claim 41, further comprising:

directing at least a portion of the effluent to a fractionator, and transferring heat from at least a portion of the effluent from the fractionator to the feedstock.

84. The method of claim 61, further comprising:

directing at least a portion of the effluent to a fractionator, and transferring heat from at least a portion of the effluent from the fractionator to the feedstock.

85. A process for converting an oxygenate to olefins, the process comprising:

providing a feedstock comprising the oxygenate, converting at least a portion of the oxygenate into an olefin-containing effluent in an oxygenate conversion reactor, transferring heat from at least a portion of the effluent to the feedstock to cause at least a portion of the feedstock to vaporize and form a vaporized feedstock, wherein the transferring heats the feedstock from a first temperature to a second temperature, quenching the effluent with a medium at an initial temperature and in an amount sufficient for forming a light product fraction and a heavy product fraction wherein the light product fraction comprises light olefins and the heavy product fraction has a final temperature which is higher than the first temperature by at least about 5° C., fractionating at least a portion of the effluent in a fractionator under conditions effective to form a plurality of fractionated streams, and heating the feedstock with at least one of the fractioned streams.

86. The method of claim 85, wherein the feedstock has a boiling range of no greater than about 30° C.

* * * * *